US006471844B1

(12) United States Patent
Samuels et al.

(10) Patent No.: US 6,471,844 B1
(45) Date of Patent: Oct. 29, 2002

(54) PROCESS FOR THE ISOLATION OF AROMATIC HYDROXYCARBOXYLIC ACIDS

(75) Inventors: Michael Robert Samuels, Wilmington, DE (US); Ronald M. Yabroff, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/743,337

(22) PCT Filed: Jul. 7, 1999

(86) PCT No.: PCT/US99/15305

§ 371 (c)(1),
(2), (4) Date: Apr. 6, 2001

(87) PCT Pub. No.: WO00/01653

PCT Pub. Date: Jan. 13, 2000

Related U.S. Application Data

(60) Provisional application No. 60/091,885, filed on Jul. 7, 1998.

(51) Int. Cl.[7] ................................................. B01D 61/44
(52) U.S. Cl. .................... 204/529; 204/530; 204/541
(58) Field of Search ................................. 204/529, 530, 204/541

(56) References Cited

U.S. PATENT DOCUMENTS 4,092,230 A 5/1978 Norton
5,282,939 A * 2/1994 Voss ........................... 204/529

FOREIGN PATENT DOCUMENTS

| GB | 1030969 | | 5/1966 |
| JP | 64-9954 | A | 1/1989 |
| JP | 4-11492 | A | 1/1992 |
| WO | WO93/25299 | A1 | 12/1993 |
| WO | WO93/25299 | * | 12/1993 |
| WO | WO97/37751 | A1 | 10/1997 |
| WO | WO97/37751 | * | 10/1997 |

OTHER PUBLICATIONS

Hakushi et al., Ion–exchange membranes XXIV. Electrodialytic concentration of carboxylic acids using ion–exchange resins, STN Chemical Abstracts, Jan. 1, 1974, vol. 4(141) XP002121544.
Lindsey, A. S., et al., The Kolbe–Schmitt Reaction, Chem. Rev., vol. 57, pp. 583–620.
International Search Report (PCT/US99/15305) dated Jul. 7, 1999.

* cited by examiner

Primary Examiner—Arun S. Phasge
(74) Attorney, Agent, or Firm—Bart E. Lerman

(57) ABSTRACT

Processes are provided for the electrodialysis of a (di)alkali metal salt of an aromatic hydroxycarboxylic acid to produce a free aromatic hydroxycarboxylic acid and the alkali metal hydroxide, in the presence of a selected alkali metal salt. These various embodiments represent efficient and economical methods for recovering the alkali metal hydroxide, as well as the parent organic compound, from these dialkali metal salts. These processes also desirably prevent overvoltage during the electrodialysis.

12 Claims, 1 Drawing Sheet

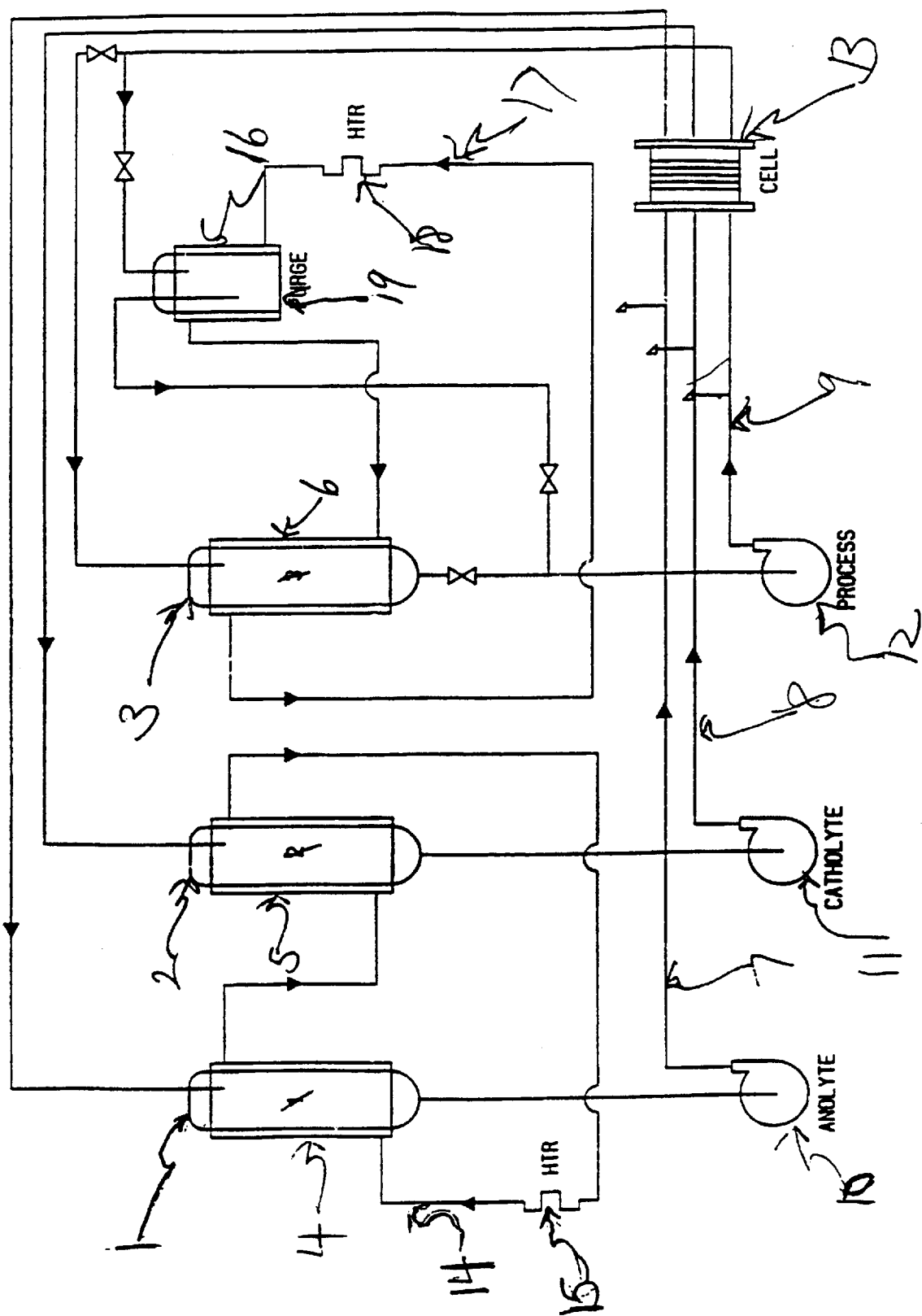

PROCESS FOR THE ISOLATION OF AROMATIC HYDROXYCARBOXYLIC ACIDS

This application claims the benefit of provisional application No. 60/091,885 filed on Jul. 7, 1998.

FIELD OF THE INVENTION

This invention relates to a process for the isolation of an aromatic hydroxycarboxylic acid from its mono- or dialkali metal salts. More particularly, this invention relates to such a process in which these salts are electrodialyzed in the presence of other selected alkali metal salts to reduce overvoltage near the end of the electrolysis. Alkali metals and their hydroxides may be completely and economically recycled in the process.

BACKGROUND OF THE INVENTION

Aromatic hydroxycarboxylic acids and dicarboxylic acids are important components in the manufacture of commercial products. For example, p-hydroxybenzoic acid (PHBA) is used to make parabens and is also used as a monomer in making polyesters, and salicyclic acid (o-hydroxybenzoic acid) is used to make aspirin. Traditionally, aromatic hydroxycarboxylic acids are manufactured using the Kolbe-Schmitt reaction, which is a reaction of an alkali metal salt of an aromatic hydroxy compound with carbon dioxide, usually under elevated temperature and pressure. The Kolbe-Schmitt reaction has been a standard procedure for the preparation of aromatic hydroxy acids for over 100 years; see for instance A. S. Lindsey, et al., Chem. Rev., vol. 57, p. 583–620 (1957) incorporated by reference herein. However, this process is complex and difficult to run, involving several manufacturing steps, which adds to the cost of the final product. Since the initial product of the carboxylation reaction is a dialkali metal salt of the aromatic hydroxycarboxylic acid, substantial cost is usually incurred for the use of compounds such as NaOH or KOH. These compounds are subsequently discarded (as sodium or potassium salts), since the free aromatic hydroxycarboxylic acid is usually isolated by reacting the dialkali metal salt with a strong acid. The dialkali metal salt of a hydroxycarboxylic acid may also be completely electrodialyzed to the free aromatic hydroxycarboxylic acid, but when one tries to completely electrodialyze these compounds (and as one approaches complete electrolysis), the voltage increases and the current efficiency decreases rapidly. As a result, the process may become impractical and/or uneconomical. Japanese Patent Application 40-11492 describes the electrodialysis of an alkali metal salt of terephthaiic acid to terephthalic acid and an alkali metal hydroxide. Japanese Patent Application 64-9954 describes the electrodialysis of an alkali metal salt of hydroxybenzoic acid.

None of the above references describes an electrodialysis in which an alkali metal salt is added to prevent overvoltage. Therefore, it would be desirable to improve these electrodialysis processes by reducing or eliminating the overvoltage without adversely affecting their advantages.

SUMMARY OF THE INVENTION

There is disclosed and claimed herein a process for the preparation of an aromatic hydroxycarboxvlic acid from its dialkali metal salt, comprising electrodialyzing an aqueous solution of a first compound of the formula $(OR^1CO_2)H_tM_{2-t}$, and a second compound of the formula $M_xH_zQ$, to produce a third compound of the formula $(OR^1CO_2)H_yM_{2-y}$ and MOH, wherein:

$R^1$ is arylene;
t is zero to about 1.90;
each M is independently an alkali metal cation;
$H_zQ$ is an anion whose conjugate acid has a $pK_a$ of about 2 or less;
x is an integer of 1 or more, and z is 0 or an integer of 1 or more, provided that x+z is equal to the total number of negative charges on Q;
M has a concentration associated with $H_zQ$ at a pH of 2.5 of about 0.03 to about 4 molar; and
y is about 1.95 to 2.00.

BRIEF DESCRIPTION OF THE DRAWINGS

The invention can be more fully understood upon having reference to the accompanying drawing.

FIG. 1 is a front elevational view of the apparatus and their layout as used in the Example and Comparative Example disclosed herein.

DETAILED DESCRIPTION OF THE INVENTION

The product of the inventive process described herein is an aromatic hydroxycarboxylic acid. The term "aromatic hydroxycarboxylic acid" as used herein means a compound that contains at least one aromatic carbocyclic ring; and at least one hydroxyl group and one carboxyl group, both groups of which are attached to a carbon atom of an aromatic carbocyclic ring. If more than one such aromatic ring is present they may be fused, as in naphthalene, connected by a covalent bond, as in biphenyl, or connected by a divalent group, as in diphenyl ether. There may also be inert groups attached to the aromatic ring(s), such as one or more alkyl groups. Compounds which may produced by this process include p-hydroxybenzoic acid, o-hydroxybenzoic acid, 2-hydroxy-3-methylbenzoic acid, 2-hydroxy-5-methylbenzoic acid, 2,4-dihydroxybenzoic acid, and hydroxynapthoic acid. Preferred products are p-hydroxybenzoic acid, 6-hydroxy-2-napthoic acid, and o-hydroxybenzoic acid; while p-hydroxybenzoic acid is especially preferred.

The term "arylene" as used herein means a radical with two free valencies to carbon atoms of one or two aromatic rings. Further, the term "hydrocarbylene" as used herein means a divalent radical containing carbon and hydrogen. "Substituted" as used herein means one or more substitutents that do not interfere with the reactions described herein. Suitable substitutents include alkyl and halogen.

The starting material for the process of the invention is the corresponding dialkali metal salt of an aromatic hydroxycarboxylic acid or its partially acidified form of the formula $(OR^1CO_2)H_tM_{2-t}$, wherein t is 0 to about 1.90, more preferably 0 to about 1.0 and especially preferably less than about 0.1. This compound is then electrolyzed so that the value of t is increased to y which is about 1.95 to about 2.00. Preferably there will be only one alkali metal present. Sodium and potassium are the preferred alkali metals, with potassium being most preferred. These dialkali metal salts usually originate as an intermediate product of the Kolbe-Schmitt synthesis of aromatic hydroxycarboxylic acids. The Kolbe-Schmitt process starts with alkali metal hydroxides. Using the process of the present invention, an essentially closed loop process with respect to alkali metal may be envisioned.

For instance, in the Kolbe-Schmitt synthesis of salicylic acid, the primary product is usually the sodium salt of salicylic acid. In the equation below, SA is salicylate dianion.

NaSA+electrodialysis→SA+NaOH

Note that enough NaOH is produced in the process to be recycled back to the beginning of the Kolbe-Schmitt process.

Electrodialysis is a well known process, see for instance B. Elvers., et al., Ed., Ullmann's Encyclopedia of Industrial Chemistry, 5th Ed., Vol. A16, VCH Verlagsgesellschaft mbH, Weinheim, 1990, p. 209–213 and 245–250, which is incorporated by reference herein. It is believed that because alkali metal hydroxide is generated in the electrolysis processes of the present invention and organic compounds are also present, fluorinated membranes, such as Nafion® Perfluorinated Membranes (from E. I. du Pont de Nemours and Company, Wilmington, Del. U.S.A.) are particularly useful in these and other electrodialysis processes.

As the skilled artisan will understand, a three compartment cell (having cathode, center, and anode compartments) may be utilized in the process of the invention and which utilizes the dialkali metal salt of the aromatic hydroxycarboxylic acid. These starting materials are fed to the center compartment, while alkali metal hydroxide will be generated in the cathode compartment. In the anodic compartment oxygen and protons are generated, while in the center compartment the compound $(OR^1CO_2)H_yM_{2-y}$ is generated. Fresh solution of the dialkali metal salt may be added to the center compartment, and the solution of the center compartment removed, at such a rate so that "average" solute in the solution is $(OR^1CO_2)H_yM_{2-y}$, as defined herein, or two or more cells may be operated in series (the solution in the center compartment going from one cell to the next).

In the process of the invention, if any of the salts of the aromatic hydroxycarboxylic acid present in the cell has a limited solubility in water, it may be desirable to heat the cell to increase the solubility in water. Limited solubility may be encountered especially when y is greater than 1, since "free" (not being an alkali metal salt) aromatic hydroxy carboxylic acid will be present, and the free organic compound may have only very limited solubility in cool water. The pH of the solution in the center compartment is an indication of what the present value of y is in that compartment (see Comparative Example 1). When M is potassium and $R^1$ is p-phenylene it is preferred to carry out the process at a temperature of about 80° C. to about 105° C., especially when y is about 0.9 or more. More generally when y is about 0.9 or more it is also preferred to carry out the process at a temperature of about 80° C. to about 105° C.

The product of the process of the invention—an aromatic hydroxycarboxylic acid—contains up to 5 mole percent of the monopotassium salt (y=1.95). Obtaining complete electrodialysis to "pure" p-hydroxybenzoic acid may require an inordinate amount of electrical energy, so the second selected alkali metal salt is also present. In the final product of the process it is preferred that y is about 1.98 or more.

In the second alkali metal compound of the formula MxH2Q, at an actual pH of 2.5 the anion present in that compound has a conjugate acid whose $pK_a$ is about 2 or less (this pKa and the pH of the solution at 2.5 is measured in dilute solution without PHBA or its salts being present). For instance, if Q is an anion having a single negative charge, then the conjugate acid of $Q^-$ is HQ, which has a $pK_a$ of about 2 or less. However when Q is an anion which may have more than one negative charge the situation can be more complex. For instance, if Q can have 3 negative charges, potential conjugate acids are $H_3Q$, $H_2Q^-$, and $HQ^=$. Generally speaking, more protons in the conjugate acid equates to a higher acidity (and a lower $pK_a$). If Q is the ortho-phosphate anion, the $pK_a$'s are 2.1, 7.2 and 12.7. This means that if any ortho-phosphate salt were to be added to the dialkali metal salt of an aromatic hydroxycarboxylic acid the dominant phosphate salt would be $HPO_4^=$ (and perhaps even $PO_4^{\equiv}$). This is because solutions of these dialkali metal salts are generally quite basic (usually with a pH of about 9 or higher). Since the pH of the solution containing the aromatic hydroxycarboxylic acid and its salts decreases during the electrolysis, the ortho-phosphate anion present would gradually become $H_2PO_4^=$. At a pH of about 2.5 (where most aromatic hydroxycarboxylic acids are in the protonated form, i.e., not a salt) the phosphate would exist predominantly as $H_2PO_4^-$, whose conjugate acid is $H_3PO_4$. Thus at pH 2.5 the alkali metal salt present would be $MH_2PO_4$, wherein M is an alkali metal cation. Thus there would be one equivalent of alkali metal present for each equivalent of ortho-phosphate containing anion. Other useful anions include sulfate, oxalate, chloride, iodate, nitrate, and picrate (inorganic anions are preferred). Some anions may cause electrochemical side reactions at the anode. For instance, chloride may be oxidized to chlorine, which may cause other problems.

A preferred anion Q is sulfate, $SO_4^=$. Since the $pK_a$ of $HSO_4^-$ is 1.9, at a pH of 2.5 most of the anion is $SO_4^=$, and the alkali salt is $M_2SO_4$. In this case there are two equivalents of alkali metal cation present per mole of sulfate present.

Another way of stating that the anion must have a conjugate acid with a $pK_a$ of about 2 or less is that if an anion that may potentially have more than one negative charge associated with it, at least one of the conjugate acids of all the potential anions must have a $pK_a$ of about 2 or less.

As mentioned above, a certain number of alkali metal cations are associated with the anion present at pH 2.5. At this pH the concentration of alkali metal cations associated with Q should be about 0.03 to about 4 molar, preferably about 0.05 to about 1.0 molar, and with a molarity of about 0.1 to about 0.3 especially preferred. There may be additional alkali metal cations present in the solution that are associated with other anions, such as the monoanion of the aromatic hydroxycarboxylic acid.

The second alkali metal compound referenced earlier herein may be added at any time to the solution containing the aromatic hydroxycarboxylic acid or its salts, but preferably before overvoltage starts to occur from increasing resistivity of this solution. This second compound may be added to this solution before it enters the electrolysis cell. The alkali metal salt, or whatever form it is added in, should be present in sufficient amount so that as the cell approaches and reaches an actual pH of about 2.5 the concentration of alkali metal cation associated with it will be in the desired range.

This second alkali metal compound may be added directly in salt form, or in another form which will make the desired compound in situ. For instance, alkali metal sulfate may be "added" as $M_2SO_4$, $MHSO_4$ or $H_2SO_4$. If bisulfate or sulfuric acid is added to a solution of the dialkali metal salt of the aromatic hydroxycarboxylic acid it will simply partially protonate the dialkali metal salt and form sulfate anion.

After exiting the electrodialysis cell the aromatic hydroxycarboxylic acid may be isolated from the solution, for example by allowing the solution to cool and the product to precipitate. The partition coefficient for most inorganic salts of alkali metal cations between the aqueous phase and the solid aromatic hydroxycarboxylic acid is believed to greatly favor the salt remaining in the aqueous phase (although one should preferably avoid inclusions of the aqueous phase in the precipitate). This means that a relatively pure form of the aromatic hydroxycarboxylic acid can be obtained which is especially low in alkali metal ion content. After separating the aromatic hydroxycarboxylic acid from the aqueous phase, the aqueous phase (including the second alkali metal compound) may be recycled in the electrodialysis process by dissolving new dialkali salt of the aromatic hydroxycarboxylic acid in it and electrodialyzing it.

During the electrodialysis some of the second alkali metal compound may be "lost" by electrolysis. If the aqueous phase is to be recycled, some makeup alkali metal second compound may be added to the aqueous phase in order to keep the concentration of the second alkali metal compound at the desired value. This can be done before or after the dialkali metal salt of the aromatic hydroxycarboxylic acid is dissolved in the aqueous phase.

In the process of the invention it is preferred that $R^1$ is p-phenylene, o-phenylene, or 2,6-naphthylene (and p-phenylene is most preferred). It is always preferred with any hydroxycarboxylic acid that the alkali metal cation of the second compound is the same as the alkali metal cation of the dialkali metal salt of the aromatic hydroxycarboxylic acid. When $R^1$ is p-phenylene or 2,6-naphthylene it is preferred that M is potassium, and when $R^1$ is o-phenylene it is preferred that $R^1$ is sodium.

Further, the concentration of the alkali metal salt of the aromatic hydroxycarboxylic acid in the aqueous solution that is electrodialyzed is not critical, but preferably not so high that free aromatic hydroxycarboxylic acid will crystallize out in the three compartment cell. However, it is preferred that the concentration is high enough so that the solution will readily conduct electricity. It is also preferred that the solution concentration be relatively high so that isolation of the free aromatic hydroxycarboxylic acid after electrolysis is simplified. Isolation may be accomplished by cooling the solution and separating the crystallized aromatic hydroxycarboxylic acid. The filtrate containing some dissolved aromatic hydroxycarboxylic acid may be recycled back into the electrodialysis, i.e., "new" alkali metal salt may be dissolved in the filtrate and the solution electrodialyzed. A preferred concentration of alkali metal salt in solution is about 10 to about 35 percent by weight, more preferably about 12 to about 25 percent by weight, of free aromatic hydroxycarboxylic acid based on the total weight of water and free aromatic hydroxycarboxylic acid equivalent in the solution.

The invention will be more readily understood to those skilled in the art upon reference to the exapmles herein. In the Example and the Comparative Example the reported pH's are those actually measured, and are uncorrected for temperature, or activities of the various species in solution. Since there is a substantial concentration of PHBA or its salts in solution, this may be a source of error in the apparent pH that is measured, since pH electrodes are subject to such errors. In order to determine at which pH "y" attains the desired value (1.95–2.00), an electrodialysis may be run, withdrawing samples at appropriate points, and determining the value of y.

EXAMPLE 1

The electrodialysis cell used was an ElectroCell AB (S-184 00 Akersberga, Sweden) "Electro MP Cell" configured as two 3-compartment cells sharing a single double sided anode arranged in parallel with respect to both electrical and process flows (see FIG. 1). Nafion® N350 semipermeable membranes (commercially available from E. I. du Pont de Nemours and Company, Wilmington, Del. U.S.A.) were used to separate the compartments of the electrodialysis cells. The nominal thickness of the membranes was 0.25 mm and they were preconditioned to the protonated form before initial use. The effective area of each anode and cathode surface was 0.01 $m^2$. The anode was a dimensionally stable oxygen anode (DSA), and the cathodes were nickel metal plates.

In FIG. 1, the anolyte, catholyte, and process reactor flasks are labeled 1, 2, and 3, respectively, and are heated by heating jackets 4, 5, and 6, respectively. The anolyte, catholyte, and process fluids are circulated through lines 7, 8, and 9, respectively, by pumps 10, 11, and 12, respectively, through 3-compartment electrodialysis cell 13 (which represents two 3-compartment cells connected in parallel, as described above), and back to reactor flasks 1, 2, and 3, respectively. Heated fluid passing through heating jackets 4 and 5 using line 14 is heated by heater 15, while heated fluid passing through heating jacket 6 and heating jacket 16 (which beats purge tank 19) using line 17 is heated by heater 18 (pumps not shown for heating lines).

Experimental solutions were prepared as follows:

Anolyte: 1.800 l distilled water and 100 g of concentrated (100% by weight) sulfuric acid were mixed together and charged into a 3 liter jacketed glass anolyte reactor flask 1.

Catholyte: 2.123 l of distilled water were mixed with 271 g of KOH/water mixture (45 wt % KOH) and charged into a 3 liter jacketed glass catholyte reactor flask 2.

Process Fluid: 1.691 l of distilled water were mixed with 487 g of KOH/water mixture (45 wt % KOH). Next, 540 g of PHBA were slowly added into this mixture with stirring. The mixture was heated to about 50° C. to facilitate dissolution of the PHBA. When the PHBA was completely dissolved, 68 g of $KHSO_4$ dissolved into 100 ml of distilled water were added to the mixture and the resultant solution was poured into a 3l jacketed glass process reactor flask 3.

Each of the reactor flasks 1,2, and 3 was heated by circulating hot water, and had its own circulating pump 10, 11, and 12, respectively, to deliver solution to the appropriate section of the electrodialysis cell 13 as shown in FIG. 1. Circulating water temperatures were set to maintain a temperature of about 90° C. in the three reactor flasks 1,2, and 3. Two individual power supplies (not shown) permitted independent adjustment of the voltage applied to each cell of 13 in case there were significant differences in internal resistance. In this way constant current flows of 15 amperes was maintained to each cell through the length of each experiment (except for the few minutes at the end of the experiment where cell voltages increased dramatically due to gas blinding of the membranes. Under these conditions the power supply was unable to maintain the 15 amperes current flow). The pH in the process fluid reactor flask 3 was continuously monitored by a Cole-Parmer pH electrode (Model # JU-05994-27) suspended in the process fluid. Hydrogen and oxygen formed during the electrolysis were vented from high point vents (not shown) in each of their respective circulating streams (hydrogen from catholyte, oxygen form anolyte). A small amount of water was added to the reactor flask 1 at about mid point in the run to make up for losses due to electroosmotic transport of water through the semipermeable membranes.

Cell voltages and pH were recorded as a function of time as shown below:

| Elapsed Time (Min) | pH | Cell Voltage |
| --- | --- | --- |
| 10 | 6.3 | 4.73 |
| 35 | 5.95 | 4.67 |
| 65 | 5.51 | 4.72 |
| 95 | 5.12 | 4.8 |
| 125 | 4.74 | 4.97 |
| 155 | 4.42 | 5.34 |
| 185 | 3.86 | 6.16 |
| 200 | 3.29 | 6.89 |
| 215 | 2.4 | 7.28 |
| 230 | 1.62 | 7.54 |

Although some minor fluctuations in cell voltage were noted at the very end of this run, current flows of 15 amperes per cell were maintained throughout, and at no point were voltage spikes over 8 v encountered. A small amount of PHBA solids precipitated in one of the unheated circulating process lines momentarily before the current was shut off.

After electric current was shut down the heaters 18 were also shut the process solutions allowed to cool to room temperature. Solid PHBA precipitated during cooling. The solid PHBA was recovered by filtration and washing.

Comparative Example 1

The preparative technique was the same as that for Example 1 except that the process fluid was prepared by mixing 1.341 l of distilled water, 974.7 g of 45% KOH in water solution, and 540 g of PHBA in a flask. The mixture was then heated to about 50° C. and stirred until the solids were fully dissolved. The resulting solution was transferred to the reactor flask 3 as described above. No sulfate ion was present in the process fluid. Cell voltage and pH as a function of time are presented below:

| Elapsed Time (min) | pH | Cell Voltage |
| --- | --- | --- |
| 10 | 12.12 | 4.52 |
| 50 | 11.05 | 4.54 |
| 70 | 10.79 | 4.56 |
| 100 | 10.33 | 4.58 |
| 130 | 9.93 | 4.59 |
| 160 | 9.6 | 4.60 |
| 190 | 9.06 | 4.67 |
| 220 | 8.18 | 4.76 |
| 250 | 6.34 | 4.73 |
| 280 | 5.77 | 4.86 |
| 310 | 5.42 | 5.05 |
| 340 | 5.09 | 5.38 |
| 370 | 4.53 | 5.98 |
| 400 | 4.3 | 7.42 |
| 430 | 2.45 | 22.9 |
| 437 | 1.45 | 38.2 |
| 445 | 1.43 | 38.2 |
| 460 | 1.42 | 38.2 |

As the process fluid pH dropped below about 4.5 the cell voltage began to fluctuate as the power supply attempted to hold a constant 15 amperes current to each cell. These fluctuations got larger as the pH decreased, and finally as the pH dropped below 2.5 they got so severe the power supply was not able to maintain the current flow. Observation of the cell outlet flows showed the presence of many very large gas bubbles in the both the anolyte and catholyte streams as the pH dropped below 3.0. The combination of high gas generation and high cell voltage suggested that significant amounts of water vapor were generated due to the very high resistive heating that occured when the process fluid and membrane electrical conductivities fell from loss of potassium ion charge carriers. Once the cell resistance started to increase, resistive heating caused local boiling which led to information of gas bubbles which blanketed the membranes and electrodes, further increasin cell resistance, voltage, and energy dissipation rates which in turn lead to more steam bubble generation. All of this clearly shows the difficulty of not operating with added potassium or other alkali metal ion, and the waste of electricity due to overvoltage when this additional ion was not added.

What is claimed is:

1. A process for the preparation of an aromatic hydroxycarboxylic acid from its dialkali metal salt, comprising electrodialyzing an aqueous solution of a first compound of the formula $(OR^1CO_2)H_tM_{2-t}$, and a second compound of the formula $M_xH_zQ$, to produce a third compound of the formula $(OR^1CO_2)H_yM_{2-y}$ and MOH, wherein:

$R^1$ is arylene;

t is zero to about 1.90;

each M is independently an alkali metal cation;

$H_zQ$ is an anion whose conjugate acid has a $pK_a$ of about 2 or less;

x is an integer of 1 or more, and z is 0 or an integer of 1 or more, provided that x+z is equal to the total number of negative charges on Q;

M has a concentration associated with $H_zQ$ at a pH of 2.5 of about 0.03 to about 4 molar; and y is about 1.95 to 2.00.

2. The process as recited in claim 1 wherein M in said first compound, said second compound, said third compound, and MOH is the same alkali metal.

3. The process as recited in claim 2 wherein Q is sulfate.

4. The process as recited in claim 1 wherein $R^1$ is p-phenylene and M is potassium.

5. The process as recited in claim 4 wherein said concentration of M is about 0.1 to about 0.3 molar.

6. The process as recited in claim 4 wherein Q is sulfate.

7. The process as recited in claim 4 wherein y is about 1.98 to about 2.00.

8. The process as recited in claim 1 wherein $R^1$ is o-phenylene and M is sodium, or $R^1$ is 2,6-naphthylene and M is potassium.

9. The process as recited in claim 8 wherein Q is sulfate.

10. The process as recited in claim 1 wherein Q is sulfate.

11. The process as recited in claim 10 wherein said sulfate is added as sulfuric acid, potassium bisulfate, or potassium sulfate.

12. The process as recited in claim 1 wherein said second compound is recycled in aqueous solution through said process.

\* \* \* \* \*